United States Patent
Addison et al.

(10) Patent No.: US 12,144,601 B2
(45) Date of Patent: Nov. 19, 2024

(54) IMPEDANCE MEASURING PROBE AND BIOPSY APPARATUS

(71) Applicant: C. R. Bard, Inc., Franklin Lakes, NJ (US)

(72) Inventors: Jordan P. Addison, Chandler, AZ (US); Scott D. Colmyer, Chandler, AZ (US); Aseem Singh, Tempe, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 271 days.

(21) Appl. No.: 16/763,140

(22) PCT Filed: Dec. 15, 2017

(86) PCT No.: PCT/US2017/066660
§ 371 (c)(1),
(2) Date: May 11, 2020

(87) PCT Pub. No.: WO2019/117943
PCT Pub. Date: Jun. 20, 2019

(65) Prior Publication Data
US 2020/0390363 A1   Dec. 17, 2020

(51) Int. Cl.
*A61B 5/0538* (2021.01)
*A61B 5/00* (2006.01)
*A61B 10/02* (2006.01)

(52) U.S. Cl.
CPC .......... *A61B 5/0538* (2013.01); *A61B 5/6848* (2013.01); *A61B 10/0233* (2013.01)

(58) Field of Classification Search
CPC ................ A61B 5/6848–685; A61B 2010/045
See application file for complete search history.

(56) References Cited

U.S. PATENT DOCUMENTS

| 5,449,370 A | 9/1995 | Vaitekunas |
| 6,103,033 A | 8/2000 | Say et al. |

(Continued)

FOREIGN PATENT DOCUMENTS

| CN | 102307529 A | 1/2012 |
| CN | 102348418 A | 2/2012 |

(Continued)

OTHER PUBLICATIONS

CN Office Action dated Oct. 29, 2023 pertaining to CN Application 201780097727.8.

*Primary Examiner* — Benjamin S Melhus
*Assistant Examiner* — Nidhi N Patel
(74) *Attorney, Agent, or Firm* — Dinsmore & Shohl LLP

(57) ABSTRACT

An impedance measuring probe for use in a biopsy apparatus includes a metal elongate member having an elongate surface, a proximal end portion, and a distal end portion. The elongate surface has a recessed longitudinal channel having a depth that longitudinally extends from the proximal end portion into the distal end portion. A conductive wire electrode, having a connection end and a sensing end, is located in and extends along the recessed longitudinal channel. The connection end extends from the proximal end portion of the elongate member and the sensing end is located at the distal end portion of the elongate member. An insulation material is disposed in the recessed longitudinal channel of the elongate member and around the conductive wire electrode so as to electrically insulate the conductive wire electrode, and with the sensing end of the conductive wire electrode being exposed.

13 Claims, 5 Drawing Sheets

(56) References Cited

U.S. PATENT DOCUMENTS

| | | | |
|---|---|---|---|
| 6,264,618 B1 | 7/2001 | Landi et al. | |
| 6,560,472 B2 | 5/2003 | Hill et al. | |
| 6,770,070 B1 | 8/2004 | Balbierz | |
| 6,892,438 B1 | 5/2005 | Hill et al. | |
| 6,913,579 B2 | 7/2005 | Truckai et al. | |
| 7,010,356 B2 | 3/2006 | Jog et al. | |
| RE40,388 E | 6/2008 | Gines | |
| 7,670,328 B2 | 3/2010 | Miller | |
| 7,756,588 B2 | 7/2010 | Jog et al. | |
| 7,850,620 B2 | 12/2010 | Miller et al. | |
| 8,220,783 B2 | 7/2012 | Gebara | |
| 8,273,227 B2 | 9/2012 | Say et al. | |
| 8,328,738 B2 | 12/2012 | Frankhouser et al. | |
| 8,414,580 B2 | 4/2013 | Rioux et al. | |
| 8,475,464 B2 | 7/2013 | Gisep et al. | |
| 8,668,698 B2 | 3/2014 | Miller et al. | |
| 8,715,287 B2 | 5/2014 | Miller | |
| 8,755,859 B2 | 6/2014 | Lang | |
| 8,777,871 B2 | 7/2014 | Frankhouser et al. | |
| 8,777,944 B2 | 7/2014 | Frankhouser et al. | |
| 8,870,865 B2 | 10/2014 | Frankhouser et al. | |
| 8,894,654 B2 | 11/2014 | Anderson | |
| 8,944,069 B2 | 2/2015 | Miller et al. | |
| 9,072,543 B2 | 7/2015 | Miller et al. | |
| 9,314,228 B2 | 4/2016 | Miller | |
| 9,393,031 B2 | 7/2016 | Miller | |
| 9,439,667 B2 | 9/2016 | Miller | |
| 9,451,968 B2 | 9/2016 | Miller et al. | |
| 9,474,894 B2 | 10/2016 | Mercanzini et al. | |
| 9,521,972 B2 | 12/2016 | Kawamoto | |
| 9,549,708 B2 | 1/2017 | Mercanzini et al. | |
| 2002/0055689 A1* | 5/2002 | Kaplan | A61B 10/0233 600/567 |
| 2002/0198470 A1* | 12/2002 | Imran | A61B 5/4255 600/587 |
| 2005/0070894 A1* | 3/2005 | McClurken | A61B 18/1492 606/50 |
| 2006/0079774 A1 | 4/2006 | Anderson | |
| 2009/0204021 A1 | 8/2009 | Shabaz | |
| 2010/0286507 A1 | 11/2010 | Paassilta et al. | |
| 2010/0317962 A1* | 12/2010 | Jenkins | A61M 25/01 600/411 |
| 2011/0230735 A1* | 9/2011 | Wolfe | A61B 5/14503 600/309 |
| 2011/0313316 A1 | 12/2011 | Ranpura | |
| 2012/0123296 A1 | 5/2012 | Hashimshony et al. | |
| 2013/0096455 A1 | 4/2013 | Kassab | |
| 2013/0096561 A1 | 4/2013 | Miller et al. | |
| 2013/0131546 A1 | 5/2013 | Azimpoor et al. | |
| 2013/0204124 A1 | 8/2013 | Duindam et al. | |
| 2014/0257265 A1 | 9/2014 | Godara et al. | |
| 2014/0276839 A1 | 9/2014 | Forman et al. | |
| 2014/0343454 A1 | 11/2014 | Miller et al. | |
| 2015/0073357 A1 | 3/2015 | Bagwell et al. | |
| 2015/0216557 A1 | 8/2015 | Mulvihill et al. | |
| 2015/0230823 A1 | 8/2015 | Morgan et al. | |
| 2015/0272667 A1 | 10/2015 | Govari | |
| 2016/0081585 A1 | 3/2016 | Halter | |
| 2016/0175543 A1 | 6/2016 | Frankhouser et al. | |
| 2016/0206346 A1 | 7/2016 | Miller | |
| 2016/0317133 A1 | 11/2016 | Orts | |
| 2016/0374723 A1 | 12/2016 | Frankhouser et al. | |
| 2017/0007271 A1 | 1/2017 | Miller et al. | |

FOREIGN PATENT DOCUMENTS

| | | |
|---|---|---|
| CN | 105228532 B | 4/2018 |
| CN | 104939916 B | 12/2019 |
| WO | 2016198910 A1 | 12/2016 |

* cited by examiner

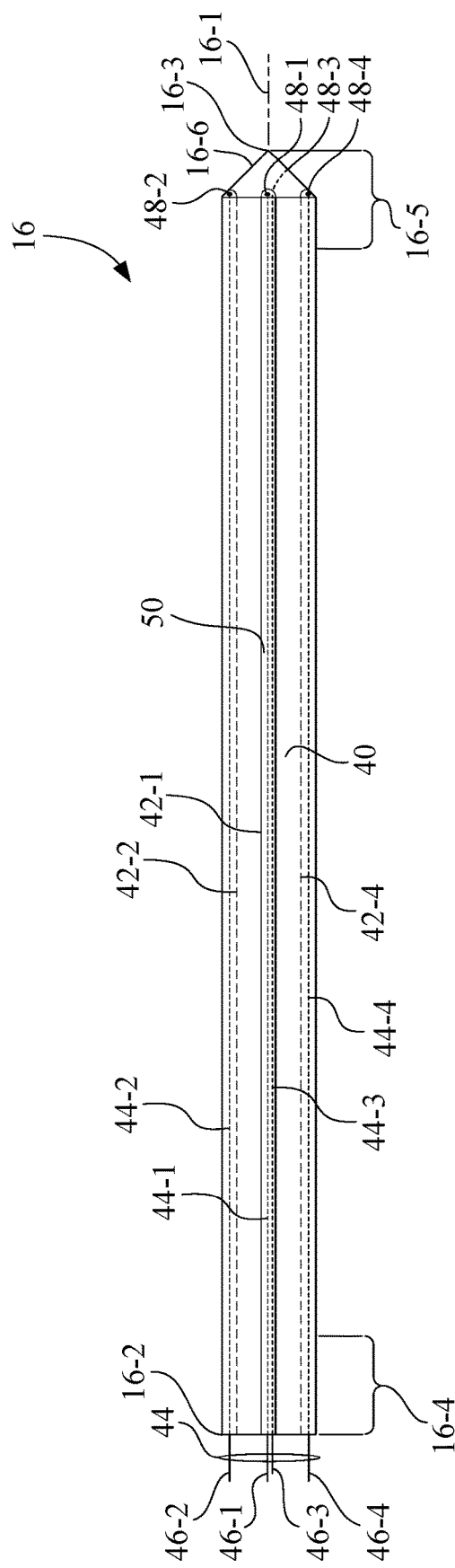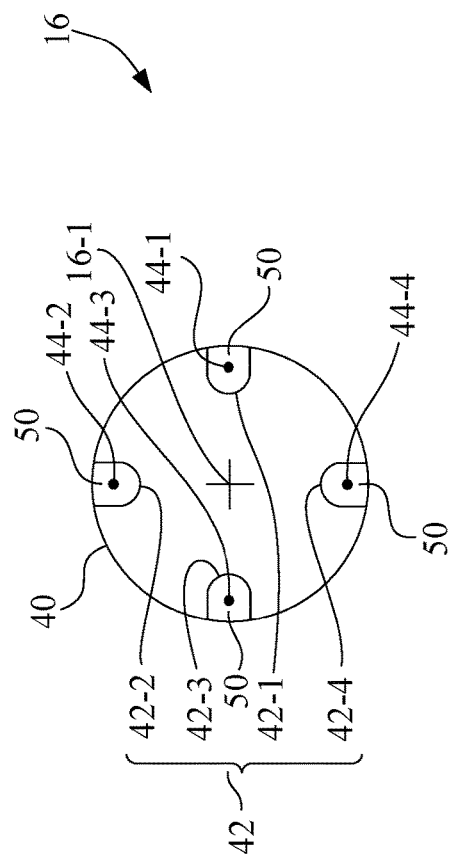
Fig. 5A
Fig. 5B

IMPEDANCE MEASURING PROBE AND BIOPSY APPARATUS

CROSS-REFERENCE TO RELATED APPLICATIONS

This application is a U.S. national phase of International Application No. PCT/US2017/066660, filed Dec. 15, 2017, which is incorporated herein by reference in its entirety.

TECHNICAL FIELD

The present invention relates to biopsy devices, and, more particularly, to a biopsy device having a probe for measuring tissue impedance.

BACKGROUND ART

A biopsy may be performed on a patient to help in determining whether the tissue in a region of interest includes cancerous cells. One biopsy technique involves inserting a biopsy probe into the tissue region of interest to capture one or more tissue samples from the region. Such a biopsy technique often utilizes a sharp probe to penetrate tissue adjacent to, or in, the tissue region of interest, after which a tissue sample is collected. Efforts continue in the art to improve the ability of the biopsy device to monitor the tissue penetration aspects of collecting a tissue sample.

What is needed in the art is a biopsy apparatus having a biopsy probe for measuring tissue impedance, to facilitate tissue type determination and/or penetration depth measurements.

SUMMARY OF INVENTION

The present invention provides a biopsy apparatus having a biopsy probe for measuring tissue impedance to facilitate tissue type determination and/or penetration depth measurements.

The invention, in one form, is directed to an impedance measuring probe for use in a biopsy apparatus. The impedance measuring probe includes a metal elongate member having a longitudinal axis, an elongate surface, a proximal end, a distal end, a proximal end portion that extends distally from the proximal end, and a distal end portion that extends proximally from the distal end. The elongate surface has a recessed longitudinal channel having a radial depth that longitudinally extends from the proximal end portion into the distal end portion. A conductive wire electrode, having a connection end and a sensing end, is located in and extends along the recessed longitudinal channel. The connection end extends from the proximal end portion of the metal elongate member and the sensing end is located at the distal end portion of the metal elongate member. An insulation material is disposed in the recessed longitudinal channel of the metal elongate member and around the conductive wire electrode so as to electrically insulate the conductive wire electrode. The sensing end of the conductive wire electrode is exposed at the distal end portion of the metal elongate member.

The invention in another form is directed to a biopsy apparatus. The biopsy apparatus includes a biopsy driver having a housing that carries a controller circuit and a motor. The controller circuit is electrically and communicatively coupled to the motor. The motor has a motor shaft. An elongate metal stylet has an elongate surface, a proximal end, a distal end, a proximal end portion that extends distally from the proximal end, and a distal end portion that extends proximally from the distal end. The proximal end portion is drivably coupled to the motor shaft of the motor. The elongate surface has a plurality of recessed longitudinal channels that extends from the proximal end portion and into the distal end portion. Each recessed longitudinal channel of the plurality of recessed longitudinal channels has a radial depth. At least one conductive wire electrode is positioned in each channel of the plurality of recessed longitudinal channels, wherein each conductive wire electrode is located in and extends along a respective recessed longitudinal channel of the plurality of recessed longitudinal channels. Each conductive wire electrode has a connection end that extends from the proximal end portion of the elongate metal stylet and has a sensing end that is located in the distal end portion of the elongate metal stylet. The connection end is electrically connected to the controller circuit. Insulation material is disposed in the plurality of recessed longitudinal channels of the elongate metal stylet and around each respective conductive wire electrode so as to electrically insulate each respective conductive wire electrode. The sensing end of each respective conductive wire electrode is exposed at the distal end portion of the elongate metal stylet.

The invention in another form is directed to an impedance measuring probe arrangement for use with a biopsy apparatus. The impedance measuring probe includes a tubular member having a tubular side wall that has a first proximal end, a first distal end, and a first distal end portion that extends proximally from the first distal end. The tubular side wall defines a lumen. An elongate metal stylet is positioned in the lumen. The elongate metal stylet has a second proximal end, a second distal end and a second distal end portion that extends proximally from the second distal end. At least one recessed longitudinal channel is formed in one of, or both of, the tubular side wall of the tubular member and the elongate metal stylet, wherein each recessed longitudinal channel extends along a longitudinal extent of one of the tubular side wall of the tubular member and the elongate metal stylet. At least one conductive wire electrode is positioned in each recessed longitudinal channel. The conductive wire electrode is electrically insulated from the tubular member and the elongate metal stylet by insulation material. Each conductive wire electrode has a connection end and a sensing end.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 5A is an enlarged side view of the elongate stylet of the probe arrangement of FIG. 3, with the elongate stylet being configured as an impedance measuring probe.

FIG. 5B is an enlarged proximal end view of the elongate stylet of FIG. 5A.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
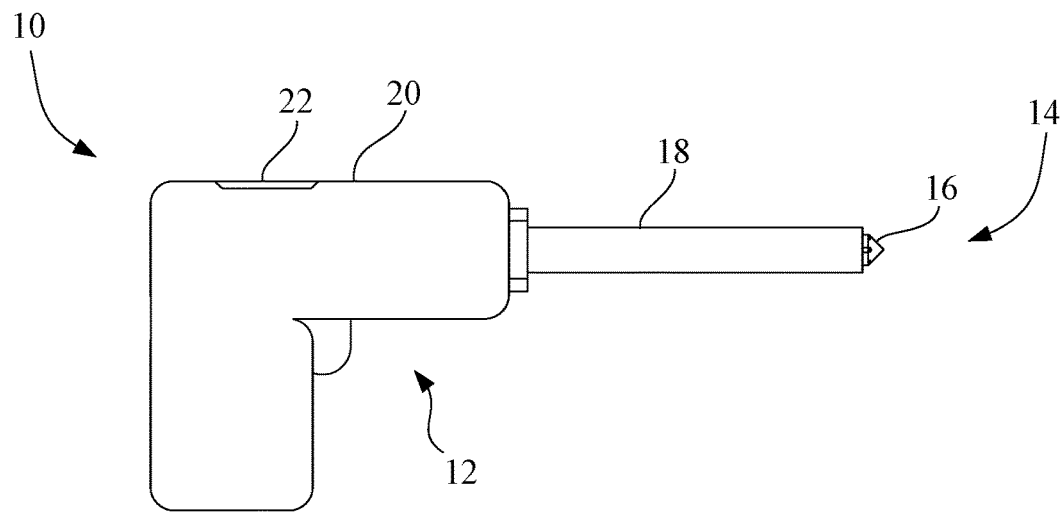
FIG. 1 is a pictorial representation of a biopsy apparatus embodying the present invention.

Referring now to the drawings, and more particularly to FIG. 1, there is shown a biopsy apparatus 10 which generally includes a biopsy driver 12 and a probe arrangement 14. In the present embodiment, probe arrangement 14 may include an elongate stylet 16 and an elongate coaxial cannula 18. In some applications, however, elongate stylet 16 may be used without coaxial cannula 18. In accordance with an aspect of the present invention, at least one component of probe arrangement 14 (e.g., the stylet, the cannula, or both the stylet and the cannula) may be configured to serve as an impedance measuring probe.

Figure 2:
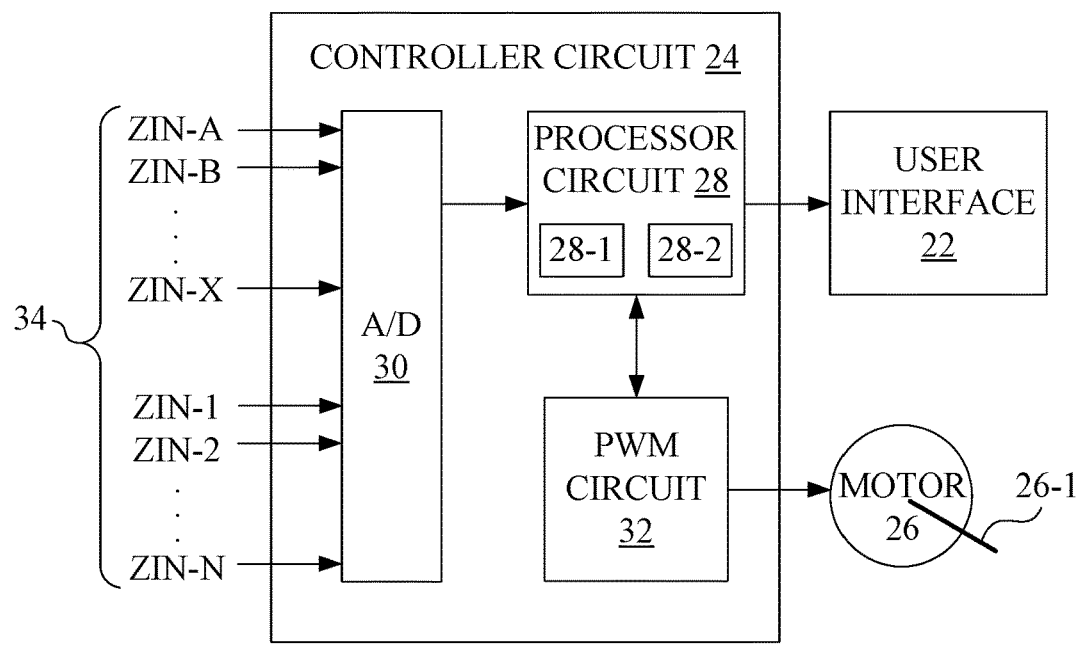
FIG. 2 is an electrical block diagram of the biopsy apparatus of FIG. 1.

Referring also to FIG. 2, biopsy driver 12 has a housing 20 that carries, e.g., contains, a user interface 22, a controller circuit 24, and a motor 26. Controller circuit 24 is electrically and communicatively coupled to each of user interface 22 and motor 26, e.g., by wires and/or circuit traces. User interface 22 may be, for example, a touch input LCD display screen. Motor 26 may be, for example, a direct current (DC) motor having a motor shaft 26-1 that is drivably coupled to elongate stylet 16 to rotate elongate stylet 16. Controller circuit 24 is configured to be electrically and communicatively coupled to the impedance measuring probe, e.g., at least one component of probe arrangement 14, as more fully described below.

As shown in FIG. 2, controller circuit 24 includes a processor circuit 28, an analog-to-digital (A/D) converter circuit 30, and a pulse width modulation (PWM) circuit 32. Processor circuit 28 is electrically and communicatively coupled to A/D converter circuit 30, PWM circuit 32, and user interface 22, e.g., by wires and/or circuit traces. Controller circuit 24 may be formed as one or more Application Specific Integrated Circuits (ASIC).

A/D converter circuit 30 includes multiple impedance input ports 34, which are grouped into two subsets, namely: impedance input ports ZIN-A, ZIN-B . . . ZIN-X and impedance input ports ZIN-1, ZIN-2 . . . ZIN-N. Impedance input ports ZIN-A, ZIN-B . . . ZIN-X may be used, for example, to receive impedance inputs for tissue impedance/composition determinations. Impedance input ports ZIN-1, ZIN-2 . . . ZIN-N may be used, for example, to receive impedance inputs for probe penetration depth determinations. Respective connection ends from the impedance measuring probe (e.g., at least one component of probe arrangement 14) are connected to the impedance input ports, either directly or via a resistive voltage divider arrangement.

Processor circuit 28 includes, for example, a microprocessor 28-1, a non-transitory electronic memory circuit 28-2, and associated circuitry, such as an input/output interface, clock, buffers, etc. Memory circuit 28-2 is a non-transitory electronic memory that may include volatile memory, such as random access memory (RAM), and non-volatile memory, such as read only memory (ROM), electronically erasable programmable ROM (EEPROM), NOR flash memory, NAND flash memory, etc.

Processor circuit 28 is configured via software and/or firmware residing in memory circuit 28-2 to execute program instructions to perform functions associated with reading the impedance at each of the multiple impedance input ports 34 of A/D converter circuit 30, and processing the various impedance inputs to generate user data, such as tissue type, to be displayed at user interface 22, and to generate motor control signals, which are supplied to PWM circuit 32. PWM circuit 32 converts the motor control signals supplied by processor circuit 28 into PWM signals which are supplied to motor 26 for controlling the revolutions-per-minute (RPMs) of motor shaft 26-1 of motor 26.

In the embodiment depicted in FIGS. 3-5B, elongate stylet 16 is configured as an impedance measuring probe and coaxial cannula 18 is a passive guide component.

Figure 3:
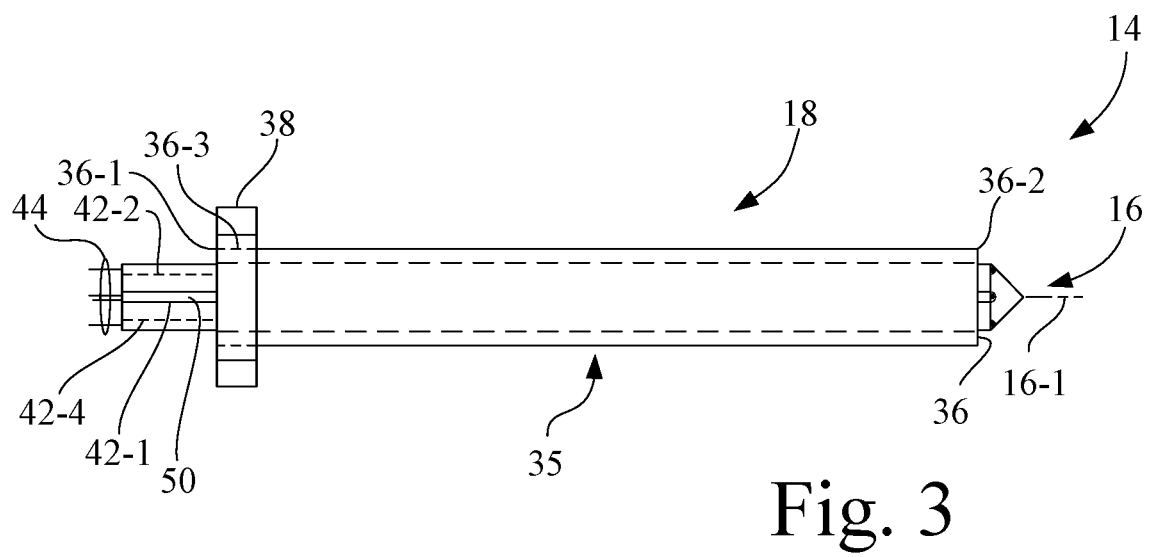
FIG. 3 is a side view of a probe arrangement of the biopsy apparatus of FIG. 1, with the elongate stylet configured as an impedance measuring probe.
Figure 4A:
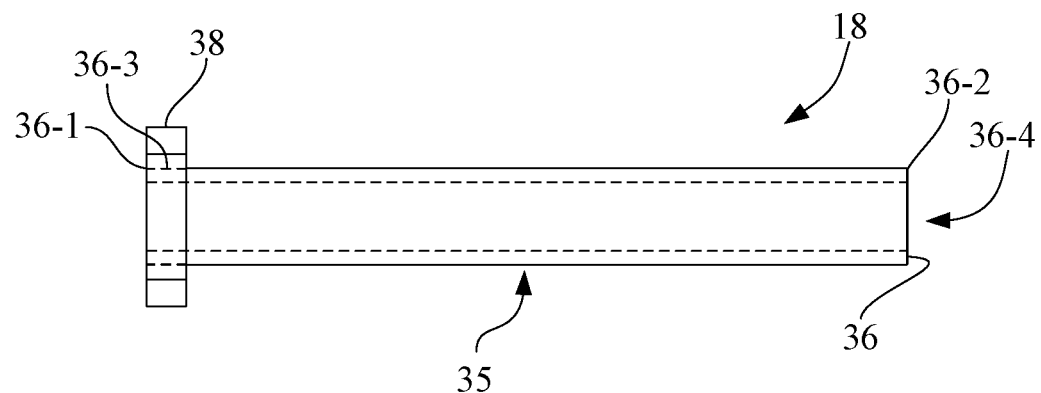
FIG. 4A is a side view of the coaxial cannula of the probe arrangement of FIG. 3.
Figure 4B:
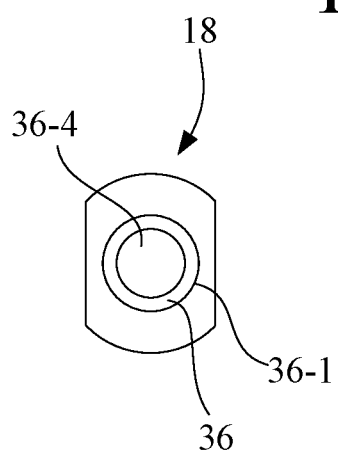
FIG. 4B is a proximal end view of the coaxial cannula of FIG. 4A.

Referring particularly to FIGS. 4A and 4B, coaxial cannula 18 includes an elongate tubular member (cannula) 35 and a hub 38. The elongate tubular member 35 has a tubular side wall 36, and may be formed from metal, such as stainless steel. Hub 38 may be formed from plastic, such as a rigid polymer. Tubular side wall 36 has a proximal end 36-1, a distal end 36-2, a proximal end portion 36-3, and a lumen 36-4. Proximal end portion 36-3 extends distally from proximal end 36-1. Hub 38 is fixedly attached, e.g., by adhesive, to proximal end portion 36-3 of tubular side wall 36. Hub 38 may serve as a user handhold and as a mounting feature for attachment to housing 20 of biopsy driver 12. Lumen 36-4 is sized to slidably receive elongate stylet 16. As shown in FIG. 3, elongate stylet 16 may be removably positioned in lumen 36-4.

Referring particularly to FIGS. 5A and 5B, in the present embodiment, elongate stylet 16 is a solid elongate member made of metal, e.g., stainless steel, having a longitudinal axis 16-1, a proximal end 16-2, a distal end 16-3, a proximal end portion 16-4 that extends distally from proximal end 16-2, e.g., a distance of one to three centimeters (cm), and a distal end portion 16-5 that extends proximally from distal end 16-3, e.g., a distance of one to five centimeters (cm). Distal end portion 16-5 includes a tapered tip portion 16-6, and distal end 16-3 is a sharp tip of the tapered tip portion 16-6 which is used to create a hole in tissue, e.g., dense tissue, such as bone. Elongate stylet 16 also includes an outer elongate surface 40. Proximal end portion 16-4 is configured to be drivably coupled to motor shaft 26-1 of motor 26 (see also FIGS. 1 and 2).

In accordance with an aspect of the present invention, outer elongate surface 40 has at least one longitudinal channel 42-1, and in the present embodiment, outer elongate surface 40 has a plurality of recessed longitudinal channels 42, individually identified as longitudinal channel 42-1, longitudinal channel 42-2, longitudinal channel 42-3, and longitudinal channel 42-4. Each of the plurality of recessed longitudinal channels 42 extends from proximal end portion 16-4 and into distal end portion 16-5, and with each recessed longitudinal channel 42-1, 42-2, 42-3, 42-4 having a radial depth, i.e., a depth in the direction toward longitudinal axis 16-1 that extends along the lengthwise extent of elongate stylet 16. The plurality of recessed longitudinal channels 42 may be formed, for example, by cutting the surface, or formed during a casting/molding process.

A plurality of conductive wire electrodes 44 is located in and extends along the plurality of recessed longitudinal channels 42. In the present example, each recessed longitudinal channel 42-1, 42-2, 42-3, 42-4 receives a respective conductive wire electrode 44-1, 44-2, 44-3, and 44-4. However, it is contemplated that in some implementations one or more of the plurality of recessed longitudinal channels 42 may carry multiple conductive wire electrodes. Conductive wire electrode 44-1 has a lengthwise extent between a connection end 46-1 and a sensing end 48-1. Conductive wire electrode 44-2 has a lengthwise extent between a connection end 46-2 and a sensing end 48-2. Conductive wire electrode 44-3 has a lengthwise extent between a connection end 46-3 and a sensing end 48-3. Conductive wire electrode 44-4 has a lengthwise extent between a connection end 46-4 and a sensing end 48-4.

Each of connection end 46-1, connection end 46-2, connection end 46-3, and connection end 46-4 extends from proximal end portion 16-4 of elongate stylet 16, and each is respectively electrically and communicatively coupled to one of the multiple impedance input ports 34 of A/D converter circuit 30 of controller circuit 24, e.g., one of impedance input ports ZIN-A, ZIN-B . . . ZIN-X and/or impedance input ports ZIN-1, ZIN-2 . . . ZIN-N (see also FIG. 2). Each of sensing end 48-1, sensing end 48-2, sensing end 48-3, and sensing end 48-4 is located at distal end portion 16-5 of elongate stylet 16. In the present embodiment, sensing end 48-1, sensing end 48-2, sensing end 48-3, and sensing end 48-4 are located at distal end portion 16-5 of elongate stylet 16, and are positioned in a circumferential arrangement at the distal end portion 16-5 of elongate stylet 16 near the distal tip at distal end 16-3 of elongate stylet 16, with the circumferential arrangement configured to provide tissue impedance information.

An insulation material 50, such as a non-conductive polymer, e.g., silicone rubber, is disposed in each recessed longitudinal channel 42-1, 42-2, 42-3, 42-4 and around the respective conductive wire electrode 44-1, 44-2, 44-3, and 44-4 so as to electrically insulate the respective conductive wire electrode 44-1, 44-2, 44-3, and 44-4 from elongate stylet 16, and from coaxial cannula 18 when elongate stylet 16 is inserted into coaxial cannula 18. Insulation material 50 encapsulates a lengthwise portion of the conductive wire electrode between the connection end and the sensing end, with the respective ends being free of insulation material to allow electrical contact or connection.

In the present embodiment, insulation material 50 fills each recessed longitudinal channel of the plurality of recessed longitudinal channels 42. The distal extent of insulation material 50 terminates prior to covering sensing end 48-1, sensing end 48-2, sensing end 48-3, and sensing end 48-4 of the plurality of conductive wire electrodes 44, such that sensing end 48-1, sensing end 48-2, sensing end 48-3, and sensing end 48-4 are exposed at distal end portion 16-5 of elongate stylet 16. Likewise, the proximal extent of insulation material 50 terminates prior to covering connection end 46-1, connection end 46-2, connection end 46-3, and connection end 46-4 of the plurality of conductive wire electrodes 44, such that connection end 46-1, connection end 46-2, connection end 46-3, and connection end 46-4 are exposed and available for connection to A/D converter circuit 30 of controller circuit 24.

Figure 6:
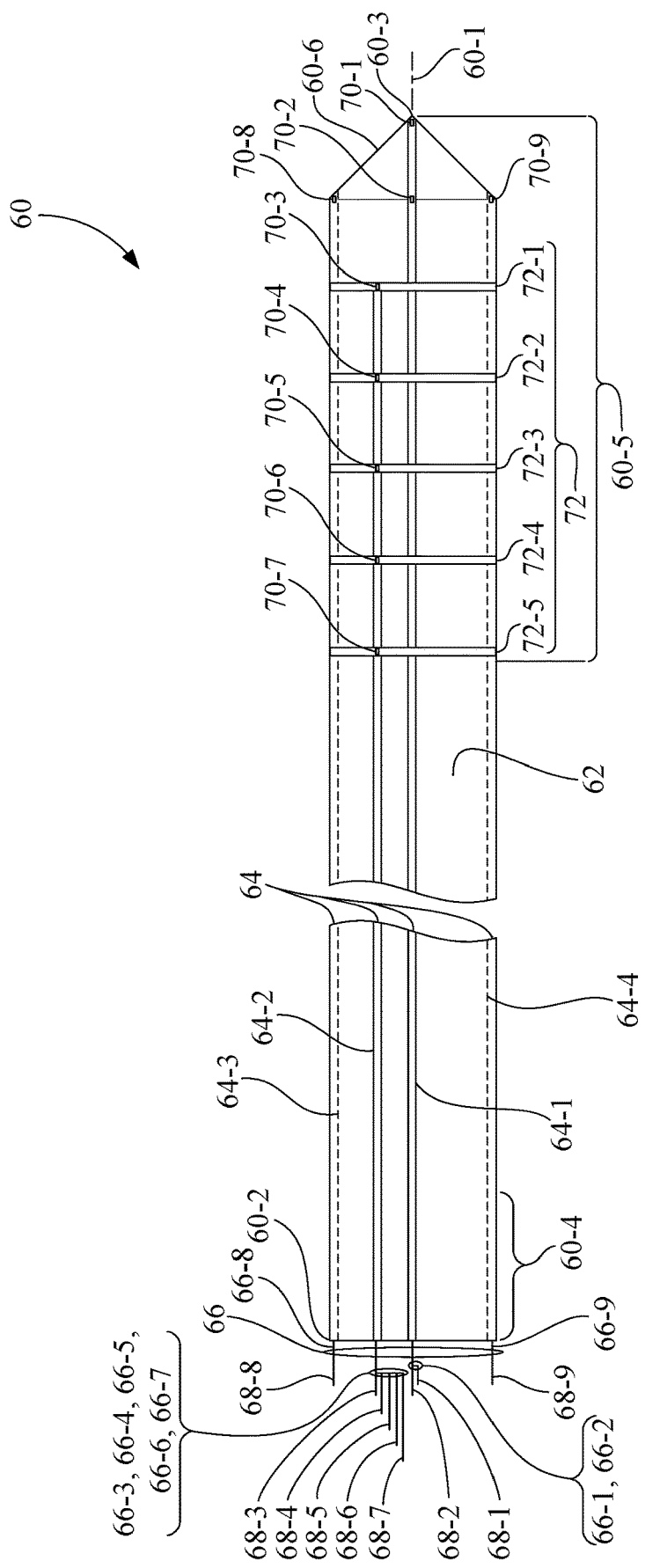
FIG. 6 is a side view of an alternative elongate stylet configured as an impedance measuring probe, having both a longitudinal arrangement and a circumferential arrangement of sensing ends of a plurality of conductive wire electrodes.

FIG. 6 shows an alternative elongate stylet 60 configured as an impedance measuring probe, which may be substituted for elongate stylet 16 of probe arrangement 14. Elongate stylet 60 may be in the form of a solid elongate member made from metal, e.g., stainless steel, having a longitudinal axis 60-1, a proximal end 60-2, a distal end 60-3, a proximal end portion 60-4 that extends distally from proximal end 60-2, e.g., a distance of one to three centimeters (cm), and a distal end portion 60-5 that extends proximally from distal end 60-3, e.g., a distance of one to five centimeters (cm). Elongate stylet 60 also includes an outer elongate surface 62. Proximal end portion 16-4 is configured to be drivably coupled to motor shaft 26-1 of motor 26 (see also FIGS. 1 and 2). Distal end portion 60-5 includes a tapered tip portion 60-6, and distal end 16-3 is a sharp tip of the tapered tip portion 60-6 which is used to create a hole in tissue, e.g., dense tissue, such as bone.

In accordance with an aspect of the present invention, elongate surface 62 has a plurality of recessed longitudinal channels 64, individually identified as longitudinal channel 64-1, longitudinal channel 64-2, longitudinal channel 64-3, and longitudinal channel 64-4. Each of the plurality of recessed longitudinal channels 64 extends from proximal end portion 60-4 and into distal end portion 60-5, and with each recessed longitudinal channel 64-1, 64-2, 64-3, 64-4 having a radial depth, i.e., a depth in a direction toward longitudinal axis 60-1 that extends along the lengthwise extent of elongate stylet 60.

A plurality of conductive wire electrodes 66 is located in and extends along the plurality of recessed longitudinal channels 64. In the present example, recessed longitudinal channel 64-1 receives conductive wire electrodes 66-1, 66-2; recessed longitudinal channel 64-2 receives conductive wire electrodes, 66-3, 66-4, 66-5, 66-6, and 66-7; recessed longitudinal channel 64-3 receives conductive wire electrode 66-8; and, recessed longitudinal channel 64-4 receives conductive wire electrode 66-9.

Conductive wire electrode 66-1 has a lengthwise extent between a connection end 68-1 and a sensing end 70-1. Conductive wire electrode 66-2 has a lengthwise extent between a connection end 68-2 and a sensing end 70-2. Conductive wire electrode 66-3 has a lengthwise extent between a connection end 68-3 and a sensing end 70-3. Conductive wire electrode 66-4 has a lengthwise extent between a connection end 68-4 and a sensing end 70-4. Conductive wire electrode 66-5 has a lengthwise extent between a connection end 68-5 and a sensing end 70-5. Conductive wire electrode 66-6 has a lengthwise extent between a connection end 68-6 and a sensing end 70-6. Conductive wire electrode 66-7 has a lengthwise extent between a connection end 68-7 and a sensing end 70-7. Conductive wire electrode 66-8 has a lengthwise extent between a connection end 68-8 and a sensing end 70-8. Conductive wire electrode 66-9 has a lengthwise extent between a connection end 68-9 and a sensing end 70-9.

Each of connection end 68-1, connection end 68-2, connection end 68-3, connection end 68-4, connection end 68-5, connection end 68-6, connection end 68-7, connection end 68-8, and connection end 68-9 extends from proximal end portion 60-4 of elongate stylet 60, and each is respectively electrically and communicatively coupled to one of the multiple impedance input ports 34 of A/D converter circuit 30 of controller circuit 24, e.g., one of impedance input ports ZIN-A, ZIN-B . . . ZIN-X and/or impedance input ports ZIN-1, ZIN-2 . . . ZIN-N.

More particularly, connection end 68-1, connection end 68-2, connection end 68-8, and connection end 68-9 are electrically and communicatively connected to impedance input ports ZIN-A, ZIN-B . . . ZIN-X of A/D converter circuit 30 of controller circuit 24 and receive impedance inputs for tissue impedance/composition determinations from sensing end 70-1, sensing end 70-2, sensing end 70-8, and sensing end 70-9. A circumferential arrangement of sensing end 70-2, sensing end 70-8, and sensing end 70-9 is located at distal end portion 60-5 of elongate stylet 60 near distal end 60-3 having the sharp distal tip. This circumferential arrangement of sensing end 70-2, sensing end 70-8, and sensing end 70-9, alone or in combination with sensing end 70-9 positioned near distal end 60-3, provides tissue impedance information to the controller circuit 24.

Connection end 68-3, connection end 68-4, connection end 68-5, connection end 68-6, and connection end 68-7 are electrically and communicatively connected to impedance input ports ZIN-1, ZIN-2 . . . ZIN-N of A/D converter circuit 30 of controller circuit 24 (see also FIG. 2) and receive impedance inputs for probe penetration depth determinations from sensing end 70-3, sensing end 70-4, sensing end 70-5, sensing end 70-6, and sensing end 70-7. A longitudinally spaced arrangement of sensing end 70-3, sensing end 70-4, sensing end 70-5, sensing end 70-6, and sensing end 70-7 is located along distal end portion 60-5 of elongate stylet 60 to provide penetration depth information to controller circuit 24.

Optionally, a longitudinally spaced arrangement of multiple circumferential metallic bands 72 may be located along a lengthwise extent of distal end portion 60-5 of elongate stylet 60 to expand the sensing area of a defined subset of the plurality of conductive wire electrodes 66. In the present embodiment, the multiple circumferential metallic bands 72 include a circumferential metallic band 72-1, a circumferential metallic band 72-2, a circumferential metallic band 72-3, a circumferential metallic band 72-4, and a circumferential metallic band 72-5. Each of the multiple circumferential metallic bands 72 surround distal end portion 60-5 of elongate stylet 60, with insulation material interposed between each of the multiple circumferential metallic bands 72 and elongate stylet 60. In the present embodiment, circumferential metallic band 72-1, circumferential metallic band 72-2, circumferential metallic band 72-3, circumferential metallic band 72-4, and circumferential metallic band 72-5 are respectively electrically connected to the longitudinally spaced arrangement of sensing end 70-3, sensing end 70-4, sensing end 70-5, sensing end 70-6, and sensing end 70-7 of conductive wire electrodes, 66-3, 66-4, 66-5, 66-6, and 66-7 to provide penetration depth information to controller circuit 24.

Figure 7A:
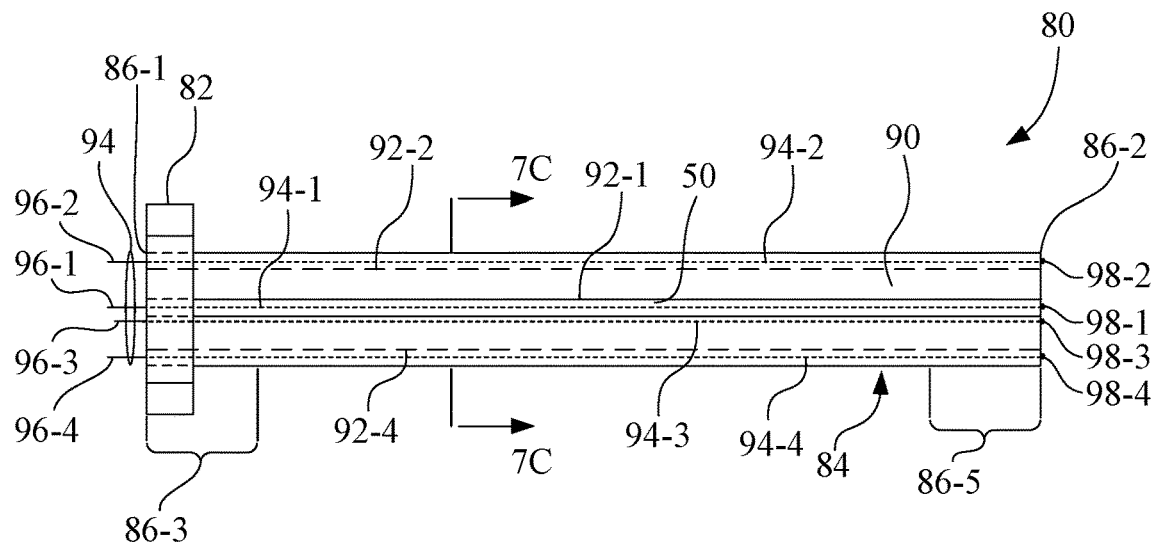
FIG. 7A is a side view of an alternative coaxial cannula that has an elongate tubular member configured as an impedance measuring probe, and having a circumferential arrangement of sensing ends of a plurality of conductive wire electrodes.
Figure 7B:
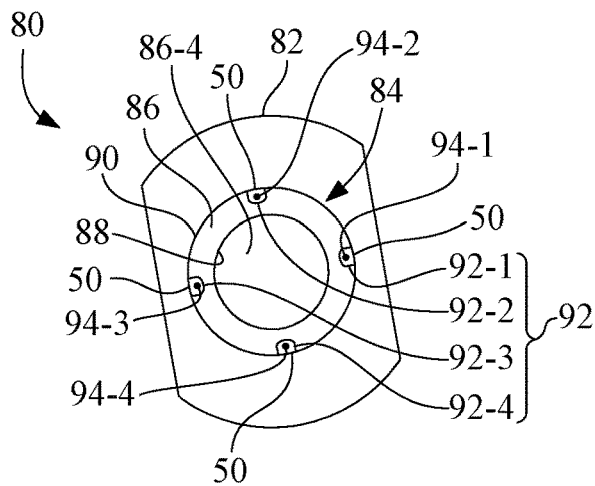
FIG. 7B is a proximal end view of the coaxial cannula of FIG. 7A.
Figure 7C:
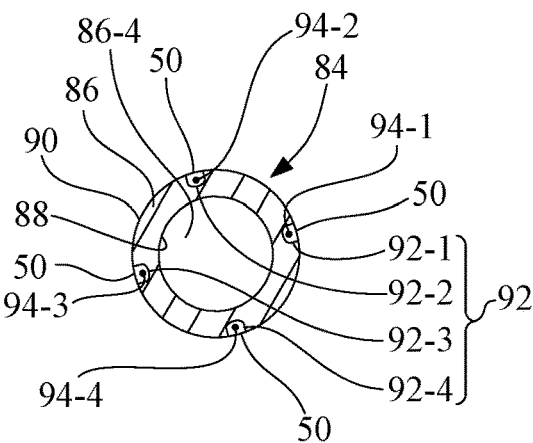
FIG. 7C is a section view of the coaxial cannula of FIG. 7A taken along line 7C-7C of FIG. 7A.

FIGS. 7A-C show an alternative configuration of a coaxial cannula that is configured as an impedance measuring probe, wherein the coaxial cannula includes one or more conductive wire electrodes. In particular, there is shown a coaxial cannula 80 having a hub 82 and a tubular member 84. Hub 82 may be formed from plastic, e.g., a rigid polymer. Tubular member (cannula) 84 is an elongate tubular structure having a tubular side wall 86, and may be formed from metal, such as stainless steel. Tubular side wall 86 has a proximal end 86-1, a distal end 86-2, a proximal end portion 86-3, a lumen 86-4, a distal end portion 86-5, an elongate interior surface 88, and an elongate exterior surface 90. Proximal end portion 86-3 extends distally from proximal end 86-1. Hub 82 is fixedly attached, e.g., by adhesive, to proximal end portion 86-3 of tubular side wall 86. Hub 82 may serve as a user handhold and as a mounting feature for attachment to housing 20 of biopsy driver 12. Lumen 86-4 is sized to slidably receive a stylet, such as one of elongate stylet 16 and elongate stylet 60, or alternatively, a passive stylet that may not include any conductive wire electrodes.

In accordance with an aspect of the present invention, elongate exterior surface 90 has at least one longitudinal channel 92-1, and in the present embodiment, elongate exterior surface 90 has a plurality of recessed longitudinal channels 92, individually identified as longitudinal channel 92-1, longitudinal channel 92-2, longitudinal channel 92-3, and longitudinal channel 92-4. Each of the plurality of recessed longitudinal channels 92 extends from proximal end portion 86-3 and into distal end portion 86-5, and with each recessed longitudinal channel 92-1, 92-2, 92-3, 92-4 having a radial depth, i.e., a depth in the direction toward lumen 86-4 that extends along the lengthwise extent of coaxial cannula 80.

A plurality of conductive wire electrodes 94 is located in and extends along the plurality of recessed longitudinal channels 92. In the present example, each recessed longitudinal channel 92-1, 92-2, 92-3, 92-4 receives a respective conductive wire electrode 94-1, 94-2, 94-3, and 94-4. However, it is contemplated that in some implementations one or more of the plurality of recessed longitudinal channels 92 may carry multiple conductive wire electrodes. Conductive wire electrode 94-1 has a lengthwise extent between a connection end 96-1 and a sensing end 98-1. Conductive wire electrode 94-2 has a lengthwise extent between a connection end 96-2 and a sensing end 98-2. Conductive wire electrode 94-3 has a lengthwise extent between a connection end 96-3 and a sensing end 98-3. Conductive wire electrode 94-4 has a lengthwise extent between a connection end 96-4 and a sensing end 98-4.

Each of connection end 96-1, connection end 96-2, connection end 96-3, and connection end 96-4 extends from proximal end portion 86-3 of tubular side wall 86, and each is respectively electrically and communicatively coupled to one of the multiple impedance input ports 34 of A/D converter circuit 30 of controller circuit 24, e.g., one of impedance input ports ZIN-A, ZIN-B . . . ZIN-X and/or impedance input ports ZIN-1, ZIN-2 . . . ZIN-N. Each of sensing end 98-1, sensing end 98-2, sensing end 98-3, and sensing end 98-4 is located at distal end portion 86-5 of coaxial cannula 80.

Insulation material 50, such as a non-conductive polymer, e.g., silicone rubber, is disposed in each recessed longitudinal channel 92-1, 92-2, 92-3, 92-4 and around the respective conductive wire electrode 94-1, 94-2, 94-3, and 94-4 so as to electrically insulate the respective conductive wire electrode 94-1, 94-2, 94-3, and 94-4 from tubular member 84 of coaxial cannula 80, and from any elongate stylet (e.g., elongate stylet 16 or elongate stylet 60) that is inserted into coaxial cannula 80. Insulation material 50 encapsulates a lengthwise portion of the conductive wire electrode between the connection end and the sensing end, with the respective ends being free of insulation material to allow electrical contact or connection.

In the present embodiment, insulation material 50 fills each recessed longitudinal channel of the plurality of recessed longitudinal channels 92. The distal extent of insulation material 50 terminates prior to covering sensing end 98-1, sensing end 98-2, sensing end 98-3, and sensing end 98-4 of the plurality of conductive wire electrodes 94, such that sensing end 98-1, sensing end 98-2, sensing end 98-3, and sensing end 98-4 are exposed at distal end portion 86-5 of coaxial cannula 80. Likewise, the proximal extent of insulation material 50 terminates prior to covering connection end 96-1, connection end 96-2, connection end 96-3, and connection end 96-4 of the plurality of conductive wire electrodes 94, such that connection end 96-1, connection end 96-2, connection end 96-3, and connection end 96-4 are exposed and available for connection to A/D converter circuit 30 of controller circuit 24 (see also FIG. 2).

Figure 8:
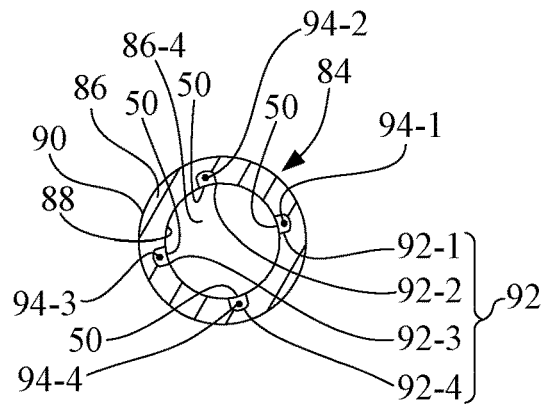
FIG. 8 shows in section view an alternative recessed channel arrangement in the tubular member of the coaxial cannula of FIG. 7A, wherein an elongate interior surface at the lumen has the plurality of recessed longitudinal channels.

FIG. 8 shows an alternative recessed channel arrangement in tubular member 84 of coaxial cannula 80, wherein elongate interior surface 88 has the plurality of recessed longitudinal channels 92, and wherein each recessed longitudinal channel 92-1, 92-2, 92-3, 92-4 receives the respective conductive wire electrode 94-1, 94-2, 94-3, and 94-4. Again, insulation material 50, such as a non-conductive polymer, e.g., silicone rubber, is disposed in each recessed longitudinal channel 92-1, 92-2, 92-3, 92-4 and around the respective conductive wire electrode 94-1, 94-2, 94-3, and 94-4 so as to electrically insulate the respective conductive wire electrode 94-1, 94-2, 94-3, and 94-4 from tubular member 84 of coaxial cannula 80, and from any elongate stylet (e.g., elongate stylet 16 or elongate stylet 60) that is inserted into coaxial cannula 80.

Further, it is contemplated that each of the elongate interior surface 88 and the elongate exterior surface 90 of tubular member 84 may have one or more of the plurality of recessed longitudinal channels 92 and one or more of the plurality of conductive wire electrodes 94.

Further, it is contemplated that each of elongate stylet 16 and elongate stylet 60 may be formed from a tubular member, such as tubular member 84 having any of the arrangements of the plurality of recessed longitudinal channels 92 described above for receiving one or more conductive wire electrodes.

In all embodiments, impedance may be measured between any two electrode sensing ends of two corresponding conductive wire electrodes, or alternatively, between a sensing end of a conductive wire electrode and a metal conductor serving as an electrical common electrical path, such as the metal elongate member, e.g., one of the elongate stylet or the tubular member of the coaxial cannula, or an electrode sensing end of a conductive wire electrode predefined to serve as a common electrical path, e.g., sensing end 70-1.

Further, in all embodiments, alternatively or supplemental to the above, it is contemplated that insulation material may be applied to, or formed on, the respective conductive wire electrode prior to insertion into a respective recessed longitudinal channel of the impedance measuring probe.

As used herein, "near" is a relative modifier intended to indicate permissible variation from the characteristic so modified. To the extent that a specific interpretation is required, for purposes of the present invention, "near" may mean less than 1.5 cm from the referenced structure.

The following items also relate to the invention:

In one form, the invention relates to an impedance measuring probe for use in a biopsy apparatus. The impedance measuring probe includes an elongate member, e.g., metal, having a longitudinal axis, an elongate surface, a proximal end, a distal end, a proximal end portion that extends distally from the proximal end, and a distal end portion that extends proximally from the distal end. The elongate surface has a recessed longitudinal channel having a radial depth that longitudinally extends from the proximal end portion into the distal end portion. A conductive wire electrode, having a connection end and a sensing end, is located in and extends along the recessed longitudinal channel. The connection end extends from the proximal end portion of the elongate member and the sensing end is located at the distal end portion of the elongate member. An insulation material is disposed in the recessed longitudinal channel of the elongate member and around the conductive wire electrode so as to electrically insulate the conductive wire electrode. The sensing end of the conductive wire electrode is exposed at the distal end portion of the elongate member. The impedance measuring probe may be configured to measure the impedance at the sensing end of the conductive wire.

Optionally, the elongate member may be a solid metal stylet having an outer surface, wherein the outer surface of the stylet is the elongate surface having the recessed longitudinal channel.

Also, optionally, the elongate member may be a tubular member having a tubular side wall that defines a lumen, an exterior surface, and an interior surface, wherein the exterior surface is the elongate surface having the recessed longitudinal channel.

Also, optionally, the elongate member may be a tubular member having a tubular side wall that defines a lumen and an interior surface, wherein the interior surface is the elongate surface having the recessed longitudinal channel.

In all of the configurations of the impedance measuring probe, the insulation material may fill the recessed longitudinal channel.

In one embodiment, a plurality of conductive wire electrodes may be located in and extends along the recessed longitudinal channel, wherein the insulation material electrically insulates the plurality of conductive wire electrodes from one another and from the metal elongate member. Each conductive wire electrode of the plurality of conductive wire electrodes has a connection end and a sensing end, with the connection end extending from the proximal end portion of the metal elongate member and the sensing end being located at the distal end portion of the metal elongate member.

In another embodiment, the elongate member has a plurality of recessed longitudinal channels that extend from the proximal end portion and into the distal end portion. Each conductive wire electrode of a plurality of conductive wire electrodes may be located in and extends along a respective recessed longitudinal channel of the plurality of recessed longitudinal channels, with each conductive wire electrode of the plurality of conductive wire electrodes having a connection end extending from the proximal end portion of the metal elongate member and a sensing end located in the distal end portion of the elongate member. Insulation material is disposed in the plurality of recessed longitudinal channels of the elongate member and around a respective conductive wire electrode of the plurality of conductive wire electrodes so as to electrically insulate the respective conductive wire electrode. The sensing end of each respective conductive wire electrode of the plurality of conductive wire electrodes is exposed at the distal end portion of the elongate member.

A circumferential arrangement of multiple sensing ends may be located at the distal end portion of the elongate member near a distal tip of the elongate member. The circumferential arrangement of the multiple sensing ends may be configured to provide tissue impedance information.

Optionally, a longitudinally spaced arrangement of multiple sensing ends may be located along the distal end portion of the elongate member. The longitudinally spaced arrangement of multiple sensing ends may be configured to provide penetration depth information.

Optionally, a longitudinally spaced arrangement of multiple circumferential metallic bands may surround the distal end portion of the metal elongate member, with insulation material interposed between the multiple circumferential metallic bands and the metal elongate member. The multiple circumferential metallic bands may be respectively electrically connected to the longitudinally spaced arrangement of multiple sensing ends.

In all embodiments, the elongate member may be one of a solid stylet and a tubular member having a tubular side wall. In all embodiments having a plurality of conductive wire electrodes, four conductive wire electrodes may be provided and/or the conductive wire electrodes may equidistantly be spaced along the circumference, optionally with an angle of 90° relative to each other.

In another form, the invention relates to a biopsy apparatus. The biopsy apparatus includes a biopsy driver having a housing that carries a controller circuit and a motor. The controller circuit is electrically and communicatively coupled to the motor. The motor has a motor shaft. An elongate stylet, i.e. metal, has an elongate surface, a proximal end, a distal end, a proximal end portion that extends distally from the proximal end, and a distal end portion that extends proximally from the distal end. The proximal end portion is drivably coupled to the motor shaft of the motor. The elongate surface has a plurality of recessed longitudinal channels that extends from the proximal end portion and into the distal end portion. Each recessed longitudinal channel of the plurality of recessed longitudinal channels has a radial depth. At least one conductive wire electrode is positioned in each channel of the plurality of recessed longitudinal channels, wherein each conductive wire electrode is located in and extends along a respective recessed longitudinal channel of the plurality of recessed longitudinal channels. Each conductive wire electrode has a connection end that extends from the proximal end portion of the elongate stylet and has a sensing end that is located in the distal end portion of the elongate stylet. The connection end is electrically connected to the controller circuit. Insulation material is disposed in the plurality of recessed longitudinal channels of the elongate stylet and around each respective conductive wire electrode so as to electrically insulate each respective conductive wire electrode. The sensing end of each respective conductive wire electrode is exposed at the distal end portion of the elongate stylet. The impedance measuring probe may be configured to measure the impedance at the sensing end of the conductive wire. In all embodiments having a plurality of conductive wire electrodes, four conductive wire electrodes may be provided and/or the conductive wire electrodes may equidistantly be spaced along the circumference, optionally with an angle of 90° relative to each other.

Optionally, a circumferential arrangement of multiple sensing ends may located at the distal end portion of the elongate metal stylet near the distal tip. The circumferential arrangement of the multiple sensing ends may be configured to provide tissue impedance information to the controller circuit.

Also, optionally, a longitudinally spaced arrangement of multiple sensing ends may be located along the distal end portion of the elongate metal stylet. The longitudinally spaced arrangement of multiple sensing ends may be configured to provide penetration depth information to the controller circuit.

As a further option, a longitudinally spaced arrangement of multiple circumferential metallic bands may surround the distal end portion of the elongate metal stylet, with insulation material interposed between the multiple circumferential metallic bands and the elongate metal stylet. The multiple circumferential metallic bands may be respectively electrically connected to the longitudinally spaced arrangement of multiple sensing ends.

The biopsy apparatus may further include a coaxial cannula having a hub and a tubular member, the tubular member having a tubular side wall having a proximal end, a distal end, and a distal end portion that extends proximally from the distal end, and the side wall defining a lumen. The elongate metal stylet may be positioned in the lumen. The tubular member may have at least one recessed longitudinal channel formed in the tubular side wall that extends along a longitudinal extent of the tubular side wall of the tubular member. In this embodiment, at least one additional conductive wire electrode may be positioned in each recessed longitudinal channel of the tubular member, and each additional conductive wire electrode may be electrically insulated from the tubular member by insulation material, and each additional conductive wire electrode has a connection end electrically connected to the controller circuit and an exposed sensing end.

In one form, the invention relates to an impedance measuring probe arrangement for use with a biopsy apparatus. The impedance measuring probe includes a tubular member having a tubular side wall that has a first proximal end, a first distal end, and a first distal end portion that extends proximally from the first distal end. The tubular side wall defines a lumen. An elongate stylet, i.e. metal, is positioned in the lumen. The elongate stylet has a second proximal end, a second distal end and a second distal end portion that extends proximally from the second distal end. At least one recessed longitudinal channel is formed in one of, or both of, the tubular side wall of the tubular member and the elongate stylet, wherein each recessed longitudinal channel extends along a longitudinal extent of one of the tubular side wall of the tubular member and the elongate stylet. At least one conductive wire electrode is positioned in each recessed longitudinal channel. The conductive wire electrode is electrically insulated from the tubular member and the elongate stylet by insulation material. Each conductive wire electrode has a connection end and a sensing end. The impedance measuring probe may be configured to measure the impedance at the sensing end of the conductive wire.

The tubular side wall may define an exterior surface and an interior surface, wherein a respective recessed longitudinal channel may be located on at least one of the exterior surface and the interior surface.

Optionally, the tubular side wall of the tubular member may have a plurality of recessed longitudinal channels and a plurality of conductive wire electrodes. Each recessed longitudinal channel of the plurality of recessed longitudinal channels has positioned therein at least one conductive wire electrode of the plurality of conductive wire electrodes, with each conductive wire electrode of the plurality of conductive wire electrodes having a connection end extending from the first proximal end portion of the tubular side wall configured for connection to a controller circuit of the biopsy apparatus and having a sensing end located in the first distal end portion of the tubular side wall. Insulation material is disposed in the plurality of recessed longitudinal channels of the tubular side wall and around each respective conductive wire electrode of the plurality of conductive wire electrodes so as to electrically insulate each respective conductive wire electrode, and wherein the sensing end of each respective conductive wire electrode of the plurality of conductive wire electrodes is exposed at the first distal end portion of the tubular side wall.

Optionally, a circumferential arrangement of multiple sensing ends may be located at the first distal end portion of the tubular side wall. The circumferential arrangement of the multiple sensing ends may be configured to provide tissue impedance information to the controller circuit.

Also, optionally, the elongate metal stylet may have a plurality of recessed longitudinal channels, and a plurality of conductive wire electrodes. Each recessed longitudinal channel of the plurality of recessed longitudinal channels has positioned therein at least one conductive wire electrode of the plurality of conductive wire electrodes, with each conductive wire electrode of the plurality of conductive wire electrodes having a connection end extending from the second proximal end portion of the elongate metal stylet configured for connection to a controller circuit of the biopsy apparatus and having a sensing end located in the second distal end portion of the elongate metal stylet. Insulation material is disposed in the plurality of recessed longitudinal channels of the tubular side wall and around each respective conductive wire electrode of the plurality of conductive wire electrodes so as to electrically insulate each respective conductive wire electrode, and wherein the sensing end of each respective conductive wire electrode of the plurality of conductive wire electrodes is exposed at the second distal end portion of the elongate metal stylet.

Optionally, a circumferential arrangement of multiple sensing ends may be located at the second distal end portion of the elongate metal stylet. The circumferential arrangement of the multiple sensing ends may be configured to provide tissue impedance information to the controller circuit.

Also, optionally, a longitudinally spaced arrangement of multiple sensing ends may be located along the second distal end portion of the metal elongate member. The longitudinally spaced arrangement of multiple sensing ends may be configured to provide penetration depth information to the controller circuit. In all embodiments having a plurality of conductive wire electrodes, four conductive wire electrodes may be provided and/or the conductive wire electrodes may equidistantly be spaced along the circumference, optionally with an angle of 90° relative to each other.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An impedance measuring probe for use in a biopsy apparatus, comprising:
a metal elongate member having a longitudinal axis, an outer elongate surface, a proximal end, a distal end, a proximal end portion that extends distally from the proximal end, and a distal end portion that extends proximally from the distal end, the outer elongate surface having a plurality of recessed longitudinal channels formed within a side wall of the outer elongate surface, the plurality of recessed longitudinal channels each having a radial depth extending toward the longitudinal axis that longitudinally extends from the proximal end portion into the distal end portion;
a plurality of conductive wire electrodes, each conductive wire electrode of the plurality of conductive wire electrodes having a connection end and a sensing end, each conductive wire electrode of the plurality of conductive wire electrodes located in and extending along the recessed longitudinal channel such that the recessed longitudinal channel encapsulates at least part of the conductive wire electrode between the connection end and the sensing end, the connection end extending from the proximal end portion of the metal elongate member and the sensing end being located at the distal end portion of the metal elongate member; and
a plurality of insulating coverings, each comprising an insulation material disposed in each of the recessed longitudinal channels of the metal elongate member and each circumferentially and longitudinally fully disposed about and encapsulating each conductive wire electrode of the plurality of conductive wire electrodes so as to electrically insulate each conductive wire electrode of the plurality of conductive wire electrodes, and with the sensing end of each conductive wire electrode of the plurality of conductive wire electrodes being exposed at the distal end portion of the metal elongate member.

2. The impedance measuring probe of claim 1, wherein the insulation material fills the recessed longitudinal channel, and wherein a cross section of each conductive wire electrode circumferentially encapsulated by each insulating covering is circular.

3. The impedance measuring probe of claim 1, wherein the insulation material electrically insulates the plurality of conductive wire electrodes from one another and from the metal elongate member.

4. The impedance measuring probe of claim 1, comprising a circumferential arrangement of multiple sensing ends located at the distal end portion of the metal elongate member near a distal tip of the metal elongate member, the circumferential arrangement of the multiple sensing ends configured to provide tissue impedance information.

5. The impedance measuring probe of claim 1, comprising a longitudinally spaced arrangement of multiple sensing ends located along the distal end portion of the metal elongate member, the longitudinally spaced arrangement of multiple sensing ends configured to provide penetration depth information.

6. The impedance measuring probe of claim 5, comprising a longitudinally spaced arrangement of multiple circumferential metallic bands that surround the distal end portion of the metal elongate member, with insulation material interposed between the multiple circumferential metallic bands and the metal elongate member, the multiple circumferential metallic bands being respectively electrically connected to the longitudinally spaced arrangement of multiple sensing ends.

7. A biopsy apparatus, comprising:
a biopsy driver having a housing that carries a controller circuit and a motor, the controller circuit being electrically and communicatively coupled to the motor, the motor having a motor shaft; and
an elongate metal stylet having a longitudinal axis, an elongate outer surface, a proximal end, a distal end, a proximal end portion that extends distally from the proximal end, and a distal end portion that extends proximally from the distal end, the proximal end portion being drivably coupled to the motor shaft of the motor, the elongate outer surface having a plurality of recessed longitudinal channels formed within a side wall of the elongate outer surface, wherein the plurality of recessed longitudinal channels extend from the proximal end portion and into the distal end portion, each recessed longitudinal channel of the plurality of recessed longitudinal channels having a radial depth extending toward the longitudinal axis;

at least one conductive wire electrode positioned in each channel of the plurality of recessed longitudinal channels, wherein each conductive wire electrode is located in and extends along a respective recessed longitudinal channel of the plurality of recessed longitudinal channels such that the respective recessed longitudinal channel encapsulates at least part of the conductive wire electrode between the connection end and the sensing end, with each conductive wire electrode having a connection end that extends from the proximal end portion of the elongate metal stylet and having a sensing end that is located in the distal end portion of the elongate metal stylet, the connection end being electrically connected to the controller circuit; and a plurality of insulating coverings, each comprising insulation material disposed in each of the plurality of recessed longitudinal channels of the elongate metal stylet and each circumferentially and longitudinally fully disposed about and encapsulating each respective conductive wire electrode so as to electrically insulate each respective conductive wire electrode, and wherein the sensing end of each respective conductive wire electrode is exposed at the distal end portion of the elongate metal stylet.

8. The biopsy apparatus of claim 7, comprising a circumferential arrangement of multiple sensing ends located at the distal end portion of the elongate metal stylet near the distal end, the circumferential arrangement of the multiple sensing ends configured to provide tissue impedance information to the controller circuit.

9. The biopsy apparatus of claim 7, comprising a longitudinally spaced arrangement of multiple sensing ends located along the distal end portion of the elongate metal stylet, the longitudinally spaced arrangement of multiple sensing ends configured to provide penetration depth information to the controller circuit.

10. The biopsy apparatus of claim 9, comprising a longitudinally spaced arrangement of multiple circumferential metallic bands that surround the distal end portion of the elongate metal stylet, with insulation material interposed between the multiple circumferential metallic bands and the elongate metal stylet, the multiple circumferential metallic bands being respectively electrically connected to the longitudinally spaced arrangement of multiple sensing ends.

11. An impedance measuring probe arrangement for use with a biopsy apparatus, comprising:
a tubular member having a tubular side wall having a first proximal end, a first distal end, and a first distal end portion that extends proximally from the first distal end, the tubular side wall defining a lumen;

an elongate metal stylet positioned in the lumen, the elongate metal stylet having a longitudinal axis, an outer elongate surface, a second proximal end, a second distal end and a second distal end portion that extends proximally from the second distal end;

a plurality of recessed longitudinal channels formed in a surface of the tubular side wall of the tubular member, wherein each recessed longitudinal channel extends along a longitudinal extent of one of the tubular side wall of the tubular member and the elongate metal stylet and each recessed longitudinal channel has a radial depth extending toward or away from the longitudinal axis;

at least one conductive wire electrode positioned in each recessed longitudinal channel, the conductive wire electrode being electrically insulated from the tubular member and the elongate metal stylet by insulation material, each conductive wire electrode having a connection end and a sensing end, wherein each recessed longitudinal channel encapsulates at least part of each of the at least one conductive wire electrodes disposed therein between the connection end and the sending end of each of the at least one conductive wire electrodes; and a plurality of insulating coverings, each comprising insulation material disposed in each of the plurality of recessed longitudinal channels of the elongate metal stylet and each circumferentially and longitudinally fully disposed about and encapsulating each respective conductive wire electrode.

12. The impedance measuring probe of claim 11, comprising:
a plurality of conductive wire electrodes, wherein each recessed longitudinal channel of the plurality of recessed longitudinal channels of the tubular side wall has positioned therein at least one conductive wire electrode of the plurality of conductive wire electrodes, with each conductive wire electrode of the plurality of conductive wire electrodes having a connection end extending from the first proximal end of the tubular side wall configured for connection to a controller circuit of the biopsy apparatus and having a sensing end located in the first distal end portion of the tubular side wall; and insulation material disposed in the plurality of recessed longitudinal channels of the tubular side wall and around each respective conductive wire electrode of the plurality of conductive wire electrodes so as to electrically insulate each respective conductive wire electrode, and wherein the sensing end of each respective conductive wire electrode of the plurality of conductive wire electrodes is exposed at the first distal end portion of the tubular side wall.

13. The impedance measuring probe arrangement of claim 11, comprising a circumferential arrangement of multiple sensing ends located at the first distal end portion of the tubular side wall, the circumferential arrangement of the multiple sensing ends configured to provide tissue impedance information to a controller circuit.

\* \* \* \* \*